United States Patent
Eder et al.

(10) Patent No.: US 8,719,978 B2
(45) Date of Patent: May 13, 2014

(54) PATIENT SUPPORT APPARATUS AND MEDICAL IMAGING APPARATUS COMPRISING THE PATIENT SUPPORT APPARATUS

(71) Applicants: Hanns Eder, Bubenreuth (DE); Patrick Gross, Langensendelbach (DE); Martin Ringholz, Erlangen (DE); Markus Schmidt, Nuremberg (DE)

(72) Inventors: Hanns Eder, Bubenreuth (DE); Patrick Gross, Langensendelbach (DE); Martin Ringholz, Erlangen (DE); Markus Schmidt, Nuremberg (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 13/776,983

(22) Filed: Feb. 26, 2013

(65) Prior Publication Data
US 2013/0219621 A1 Aug. 29, 2013

(30) Foreign Application Priority Data

Feb. 29, 2012 (DE) .......................... 10 2012 203 133

(51) Int. Cl.
*A61B 6/04* (2006.01)
*A61G 7/047* (2006.01)

(52) U.S. Cl.
USPC ....................................... 5/601; 5/606; 5/600

(58) Field of Classification Search
USPC ......... 5/601, 606, 600, 86.1, 81.1 R; 378/209
See application file for complete search history.

(56) References Cited

U.S. PATENT DOCUMENTS

| | | | | |
|---|---|---|---|---|
| 2,700,381 A * | 1/1955 | Powell | | 5/621 |
| 4,063,097 A | 12/1977 | Barrett | | |
| 5,349,965 A | 9/1994 | McCarver | | |
| 6,772,461 B2 * | 8/2004 | Gaspar | | 5/632 |
| 6,854,137 B2 * | 2/2005 | Johnson | | 5/88.1 |
| 7,000,268 B2 * | 2/2006 | Johnson | | 5/81.1 R |
| 7,540,661 B2 * | 6/2009 | Hornig | | 378/209 |
| 7,578,011 B2 * | 8/2009 | Johnson | | 5/81.1 R |
| 2001/0044967 A1 * | 11/2001 | Gaspar | | 5/632 |
| 2003/0213064 A1 * | 11/2003 | Johnson | | 5/86.1 |
| 2005/0102748 A1 * | 5/2005 | Johnson | | 5/81.1 R |
| 2006/0174405 A1 * | 8/2006 | Johnson | | 5/81.1 R |
| 2007/0003022 A1 * | 1/2007 | Hornig | | 378/209 |
| 2007/0039101 A1 | 2/2007 | Luginbuhl | | |
| 2011/0173753 A1 * | 7/2011 | Luginbuhl et al. | | 5/601 |
| 2012/0114107 A1 * | 5/2012 | Wang et al. | | 378/209 |
| 2013/0219621 A1 * | 8/2013 | Eder et al. | | 5/601 |

FOREIGN PATENT DOCUMENTS

| | | |
|---|---|---|
| DE | 4316961 A1 | 11/1994 |
| DE | 102004050385 A1 | 5/2006 |
| WO | WO 2009032933 A1 | 3/2009 |

* cited by examiner

Primary Examiner — Robert G Santos

(57) ABSTRACT

A patient support apparatus, in particular for a medical imaging apparatus, has a table for supporting a patient, and a support unit, wherein the table is arranged at the support unit such that the table may be displaced along a longitudinal extension of the support unit. Further, the patient support apparatus has a protective wall element which closes off a region for receiving fluids on the table and/or on the support unit in a fluid-tight manner.

9 Claims, 3 Drawing Sheets

PATIENT SUPPORT APPARATUS AND MEDICAL IMAGING APPARATUS COMPRISING THE PATIENT SUPPORT APPARATUS

CROSS REFERENCE TO RELATED APPLICATIONS

This application claims priority of German Patent Application No. 10 2012 203 133.2 DE filed Feb. 29, 2012. All of the applications are incorporated by reference herein in their entirety.

FIELD OF INVENTION

A patient support apparatus is provided, in particular for a medical imaging apparatus, having a table for supporting a patient, and a support unit, on which the table is supported in such a manner that it can be displaced along a longitudinal extension of the support unit.

BACKGROUND OF INVENTION

During medical imaging examinations, for example examinations using a magnetic resonance apparatus, computed tomography apparatus, AX apparatus, etc., it may happen that body fluids, for example blood, and/or medical fluids, for example Ringer's solutions and/or contrast agents and/or cooling agents, etc., are discharged and can spread onto a table of a patient support apparatus. Such fluids can also spread from said table to the medical imaging device and penetrate for example into an AX C-arm, a gantry of the computed tomography apparatus, a recording region of the magnetic resonance apparatus, etc.

Medical imaging apparatuses are tested in respect of protection against water spray but are not designed to absorb for example several liters of fluid. Therefore such fluid egress can cause unwanted damage to the medical imaging apparatuses. Provision can also be made for some medical imaging apparatuses not to be permitted for such examinations and/or applications, so that the field of use of the medical imaging apparatus is restricted.

To prevent the spread of discharged fluid within the patient support apparatus and/or within the medical imaging apparatus, until now a fluid-repelling film has been used to protect the patient support apparatus and/or the medical imaging apparatus from discharged fluid. Inserts made of an absorbent material are also known, being used to configure a contact surface of the patient support apparatus. The discharged fluids can thus be bound. However if large quantities of fluid are discharged, it is difficult to prevent the spread and/or infiltration of the fluid into the medical imaging apparatus and/or into the patient support apparatus.

SUMMARY OF INVENTION

An object is to provide a patient support apparatus, which allows a large quantity of fluid to be received and also facilitates simple cleaning. The object is achieved by the apparatuses as claimed in the independent claims. Embodiments are provided in the dependent claims.

A patient support apparatus, in particular for a medical imaging apparatus, has a table for supporting a patient, and a support unit, on which the table is supported in such a manner that it may be displaced along a longitudinal extension of the support unit.

It is proposed that the patient support apparatus has at least one protective wall element, which closes off a region for receiving fluids on the table and/or on the support unit in a fluid-tight manner. The patient support apparatus is preferably configured to support a patient for a medical imaging examination, for example a magnetic resonance apparatus, a computed tomography apparatus, an AX apparatus, etc. To this end the patient support apparatus can be formed by a patient support apparatus disposed in a fixed manner on the medical imaging apparatus or by a mobile patient support apparatus, which can have a coupling unit for coupling to the medical imaging apparatus.

An embodiment allows for a fluid, for example a body fluid of the patient, e.g. blood, and/or a medical fluid, e.g. an infusion fluid, etc., to be collected during the medical imaging examination, advantageously preventing the fluid from spreading. In particular, the patient support apparatus and/or the medical imaging apparatus may be protected from damage by spreading fluid and/or fluid infiltrating into the patient support apparatus and/or the medical imaging apparatus. This embodiment also allows the field of application of the medical imaging apparatus to be extended to include applications in which there is a high risk of body fluids of the patient and/or medical fluids, for example infusion solutions and/or contrast agent solutions, being discharged. It also allows the patient support apparatus to be cleaned in a simple manner in that cleaning is restricted to the receiving region. For example, it is possible to remove the protective wall element to clean the support unit and/or the table. Use of the at least one protective wall element also means that there is no need for an expensive and complex trough structure for receiving fluids, which can be disposed on the patient support apparatus. Fluid-tight in this context means in particular that, as a result of its embodiment and/or its arrangement within the patient support apparatus, the protective wall element forms a barrier in respect of the spread of fluids and the protective wall element cannot be penetrated by fluids.

The at least one protective wall element may be disposed on the table, in particular at the side of a support surface for supporting the patient on the table, so that discharged fluids may be held back before they spread in an unwanted manner. However, it is particularly advantageous for the support unit to have a receiving region for receiving fluids, the at least one protective wall element delimiting the receiving region for receiving fluids along the longitudinal extension in a fluid-tight manner. This allows for the receiving region to be configured for receiving larger quantities of fluid, thereby allowing an unwanted escape of fluids from the receiving region to be advantageously prevented, regardless of the quantity of fluid.

The support unit has at least two protective wall elements, which are disposed in different positions along the longitudinal extension on the support unit, allowing a receiving region for receiving fluids to be embodied on at least two sides in a fluid-tight manner. More than two protective wall elements may also be disposed on the support unit, so that, together with the support unit, in particular the receiving region, they may form a number of chambers for receiving fluids. This may be advantageous when transporting the patient support apparatus, as the chambers restrict the movement of the fluids in the chambers, thereby preventing the fluids overflowing out of the receiving region.

In a further embodiment, the support unit and/or the table has a latching unit for a latching connection between the at least one protective wall element and the support unit and/or the table. This allows the protective wall element to be disposed in a particularly simple manner on the support unit and/or the table if required. The protective wall element may also thus be removed from the support unit and/or the table, for example when cleaning the patient support apparatus.

It is further proposed that the latching unit has at least two or more latching elements, which are disposed in different positions along a longitudinal extension of the support unit, thereby allowing particularly simple mounting of the protective wall elements in different positions on the support unit.

The at least one protective wall element is formed from a fluid-tight material, with the result that the protective wall element also provides effective protection against the spread of fluids over quite a long time period. The at least one protective wall element may also be formed from a material that is easy to clean and/or can be disinfected, so that the patient support apparatus may also be cleaned in a simple and time-saving manner after a medical imaging examination during which leakage occurs. This reduces the time during which the medical imaging apparatus and/or the patient support apparatus is occupied by a patient for a medical imaging examination, thereby allowing a higher patient throughput to be achieved. The at least one protective wall element may be formed from a magnetic resonance-compatible material.

Protection against the unwanted splashing and/or overflowing of fluids held back by the protective wall element over the protective wall element may be achieved, if the protective wall element has a height, which exceeds a multiple of an expected fluid level within the receiving region for receiving fluids. If for example a base surface of the receiving region for receiving fluid is approx. 1.0 m$^2$, a quantity of fluid of approx. 2 l corresponds to a level of approx. 2 mm within the receiving region. The height of the protective wall element is at least five times an expected fluid level within the receiving region, preferably at least ten times the expected fluid level within the receiving region. The at least one protective wall element has for example a height of at least 3 cm, and preferably approx. 5 cm.

The region for receiving fluids may be configured to be leak-tight in respect of a discharge of fluids, if the at least one protective wall element has a length, which corresponds to a distance between two support rails of the support unit. The at least one protective wall element may have a sealing element, for example a sealing lip, along a peripheral region and/or edge region, so that a peripheral region and/or edge region, having a surface adjoining one of the support rails, can be configured in a fluid-tight manner.

In an embodiment, it is proposed that the patient support apparatus has at least one absorbent insertion element, which is disposed within a receiving region for receiving fluids, thereby binding a discharged fluid and thus preventing the fluid splashing and/or overflowing over the protective wall element in an unwanted manner during transportation of the patient support apparatus. It also allows a larger quantity of fluids to be received within the receiving region, without there being a risk of the fluid splashing and/or overflowing over the protective wall element during transportation.

If the patient support apparatus has a control unit, which controls an approach speed of the table and/or patient support apparatus for movement of the table and/or the patient support apparatus in such a manner that fluid is prevented from overflowing over the protective wall element, a particularly reliable patient support apparatus is provided, which may prevent the egress of fluid from a receiving region for receiving fluid even during transportation.

A medical imaging apparatus has a patient support apparatus, the patient support apparatus having a table, for supporting a patient, and a support unit, on which the table is supported in such a manner that it can be displaced along a longitudinal extension of the support unit.

The patient support apparatus has at least one protective wall element, which closes off a region for receiving fluids on the table and/or on the support unit in a fluid-tight manner. A fluid, for example a body fluid of the patient, e.g. blood, and/or a medical fluid, e.g. an infusion fluid, etc., may be collected during the medical imaging examination and the spread of the fluid may be prevented. In particular, the patient support apparatus and/or the medical imaging apparatus may hereby be protected from damage by a spreading fluid and/or a fluid infiltrating into the patient support apparatus and/or the medical imaging apparatus. This embodiment also allows the field of application of the medical imaging apparatus to be extended to include applications, in which there is a high risk of body fluids of the patient and/or medical fluids, for example infusion solutions and/or contrast agent solutions, being discharged. It is also possible to clean the patient support apparatus in a simple manner, in that cleaning is restricted to the receiving region. For example, it may be possible to remove the protective wall element to clean the support unit and/or the table.

DETAILED DESCRIPTION OF INVENTION

Figure 1:
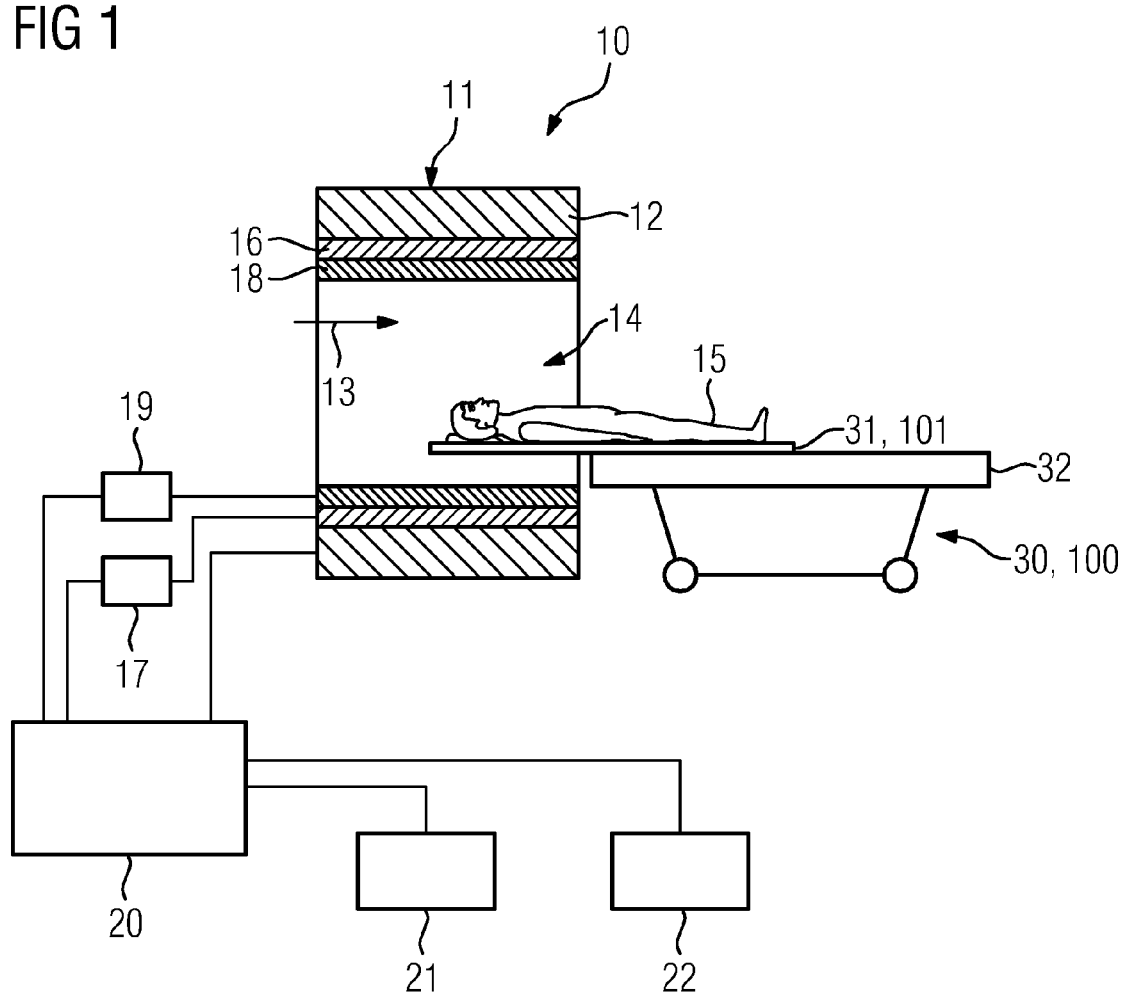
FIG. 1 shows a schematic diagram of a medical imaging apparatus.

FIG. 1 shows a schematic diagram of a medical imaging apparatus by way of example as a magnetic resonance apparatus 10. However, the embodiment of the medical imaging apparatus is not restricted to the magnetic resonance apparatus 10; the medical imaging apparatus can of course also be formed by a computed tomography apparatus, an AX apparatus, a PET apparatus, etc.

The magnetic resonance apparatus 10 comprises a magnetic unit 11 with a main magnet 12 for generating a powerful and in particular constant main magnetic field 13. The magnetic resonance apparatus 10 also has a cylindrical receiving region 14 for receiving a patient 15, the receiving region 14 being enclosed in a peripheral direction by the magnetic unit 11. The patient 15 may be introduced by a patient support apparatus 30 of the magnetic resonance apparatus 10 into the receiving region 14. The patient support apparatus 30 is disposed in a movable manner within the magnetic resonance apparatus 10.

The magnetic unit 11 also has a gradient coil 16 for generating magnetic field gradients, which is used for spatial encoding during imaging. The gradient coil 16 is controlled by means of a gradient control unit 17. The magnetic unit 11 also has a cylindrical high-frequency coil unit 18 and a high-frequency control unit 19 for stimulating polarization, which is established in the main magnetic field 13 generated by the main magnet 12. The high-frequency coil unit 18 is controlled by the high-frequency control unit 19 and emits high-frequency magnetic resonance sequences into an examination space, which is essentially formed by the receiving region 14.

This deflects the magnetization from its equilibrium position. Magnetic resonance signals are also received by means of the high-frequency coil unit 18.

To control the main magnet 12, the gradient control unit 17 and the high-frequency control unit 19, the magnetic resonance apparatus 10 has a control unit 20 formed by a computation unit. The computation unit controls the magnetic resonance apparatus 10 centrally, for example the performance of a predefined imaging gradient echo sequence. Control information, such as imaging parameters for example, and reconstructed magnetic resonance images can be displayed to an operator on a display unit 21, for example on at least one monitor, of the magnetic resonance apparatus 10. The magnetic resonance apparatus 10 also has an input unit 22, by means of which information and/or parameters may be input by an operator during a measuring operation.

The illustrated magnetic resonance apparatus 10 can of course comprise further components that are normally a feature of magnetic resonance apparatuses 10. A general mode of operation of a magnetic resonance apparatus 10 is also known to the person skilled in the art so there is no need for a detailed description of the general components here.

Figure 2:
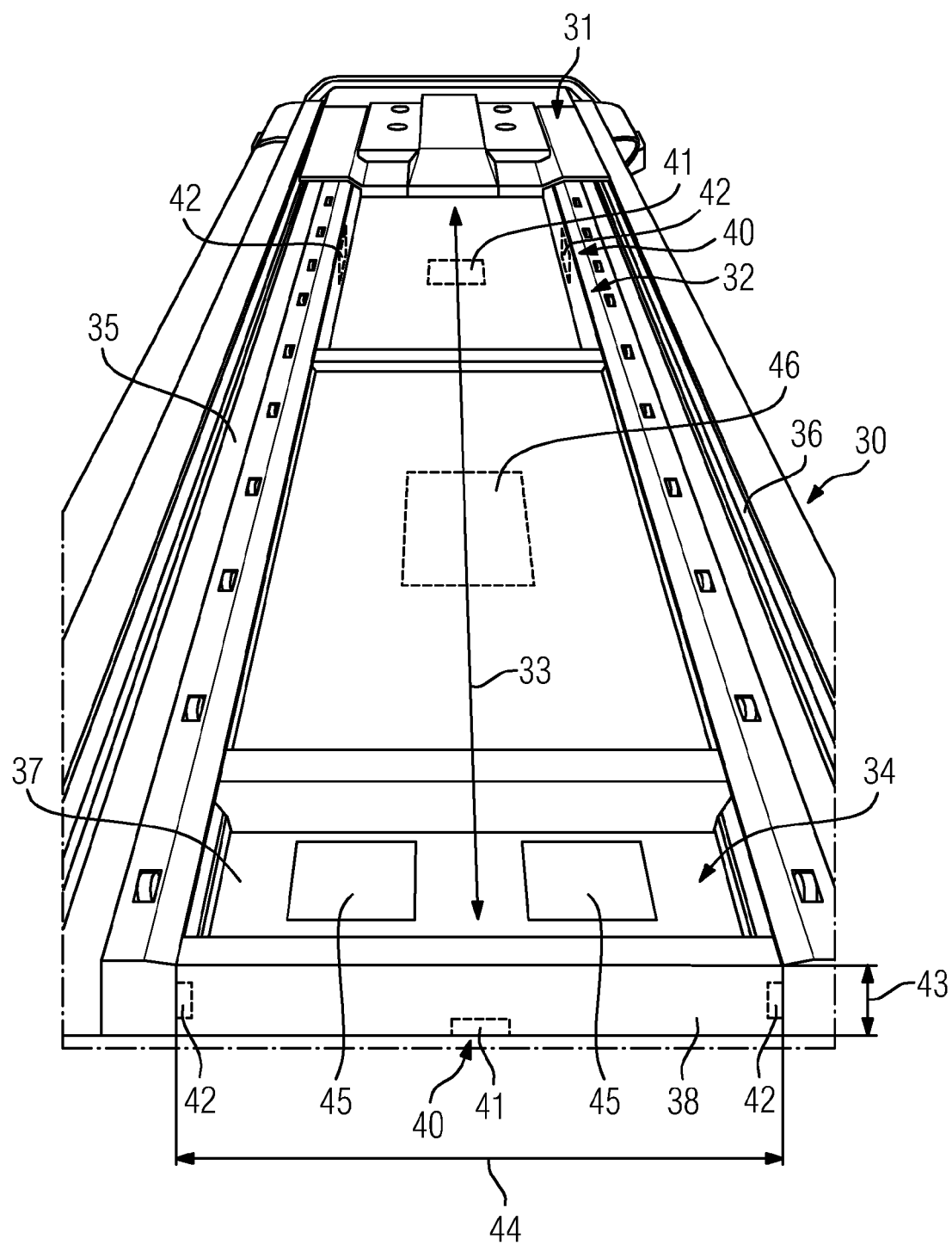
FIG. 2 shows a schematic diagram of a patient support apparatus.

The patient support apparatus 30 is shown in more detail in FIG. 2 and has a table 31 and a support unit 32. The table 31 is designed for supporting and positioning the patient 15 on the patient support apparatus 30. The support unit 32 is designed to support the table 31 on the patient support apparatus 30 in a movable and/or displaceable manner, so that the patient 15 is positioned within the receiving region 13 of the magnetic resonance apparatus 10 by displacing the table 31. The movement and/or displacement of the table 31 takes place here along a longitudinal extension 33 of the support unit 32.

The support unit 32 of the patient support apparatus 30 has a receiving region 34 for receiving fluids. The support unit 32 also has two guide rails 35, 36, which delimit the sides of the receiving region 34. The support rails 35, 36 are designed to guide the table 31 during movement of the table 31. The support unit 32 also has a lower delimiting wall 37, which delimits the receiving region 34 at the bottom, in particular in the direction of the force of its weight. The two side guide rails 35, 36 are disposed along the longitudinal extension 33 of the support unit 32 on the lower delimiting wall 37. The lower delimiting wall 37 and the two support rails 35, 36 disposed at the sides are formed here by a fluid-tight material. The table 31 has a slightly trough-shaped configuration, so that fluids discharged during a medical imaging examination can flow off into the receiving region 34 for receiving fluids.

The support unit 32 also has a number of protective wall elements 38, which delimit the receiving region 34 for receiving fluids along the longitudinal extension 33 of the support unit 32, with just one of the protective wall elements 38 being shown in FIG. 2 and the other protective wall element being concealed by the table 31.

The protective wall elements 38 close off the receiving region 34 in a fluid-tight manner along the longitudinal extension 33, so that when fluids are discharged during a medical imaging examination, in particular a magnetic resonance examination, said fluid remains enclosed within the receiving region 34 and the spreading and/or penetration of the fluid into the medical imaging apparatus and/or the patient support apparatus 30 is advantageously prevented.

The individual protective wall elements 38 here are formed from a fluid-tight material, so that any escape from the protective wall elements 38 is advantageously prevented. The fluid-tight material of the protective wall elements 38 is configured to be magnetic resonance-compatible. The individual protective wall elements 38 are also made from a material that is easy to clean and/or can be disinfected, so that it is also possible to clean the receiving region 34 in a simple manner.

To dispose the protective wall elements 38 on the support unit 32, the latter has a latching unit 40 for a latching connection between the protective wall elements 38 and the support unit 32. The latching unit 40 allows simple insertion of the individual protective wall elements 38 on the support unit 32, in particular on the lower delimiting wall 37 and/or on the side support rails 35, 36, when the protective wall elements 38 are being mounted. The latching unit 40 has a number of latching elements 41, 42, which are disposed on the support unit 32, in particular on the lower delimiting wall 37 and/or the side support rails 35, 36. Some of the latching elements 41, 42 are also disposed on the support unit 32 in different positions along the longitudinal extension 33 of the support unit 32, so that the individual protective wall elements 38 can be disposed in different positions on the support unit 32 to delimit the receiving region 34.

More than two protective wall elements 38 may also be disposed in such a manner on the support unit 32, with the individual protective wall elements 38 being disposed in different positions along the longitudinal extension 33 on the support unit 32. This allows the size of the receiving region 34 for receiving fluids to be matched to an ongoing medical imaging examination and/or the receiving region 34 for receiving fluids can be divided into individual receiving chambers, so that the overflowing and/or splashing over of the fluid present in the receiving chambers is prevented when the patient support apparatus 30 is moved and/or transported.

Alternatively, the latching elements 41, 42 are only disposed on end regions of the support unit 32 along the longitudinal extension 33 on the support unit 32, so that the protective wall elements 38 are only disposed on the end regions of the support unit 32.

Further protection against overflowing and/or splashing over of the fluid present in the receiving region 34 and/or in the receiving chambers is achieved if the protective wall elements 38 have a height 43, which exceeds a multiple of an expected fluid level within the receiving region 34 for receiving fluids. The height 43 of the protective wall elements 38 is preferably at least five times the expected fluid level and particularly preferably at least ten times the expected fluid level. The expected fluid level is defined by a base surface of the receiving region 34 for receiving fluids and a maximum expected quantity of fluid. If for example the base surface is approx. 1 m$^2$ and the maximum quantity of fluid is approx. 2 l, this would correspond to a fluid level of approx. 2 mm within the receiving region 34. The individual protective wall elements 38 have a height 43 of minimum 3 cm, preferably however a height of approx. 5 cm.

The protective wall elements 38 also have a length 44, which corresponds to a distance between the two support rails 35, 36, so that transitions at peripheral regions and/or edge regions between the protective wall elements and the support rails 35, 36 are configured as fluid-tight. The protective wall elements 38 can also have additional sealing elements, for example sealing lips, on peripheral regions and/or edge regions, which face the support rails 35, 36 and/or the lower delimiting wall 37, closing off said peripheral region and/or edge region in a fluid-tight manner. A distance between the two support rails 35, 36 corresponds essentially to a width of the table 31, so that the length 44 of the protective wall elements 38 is at least 40 cm, preferably between 45 cm and 50 cm.

Absorbent insertion elements 45 are disposed within the receiving region 34 for receiving fluids. These absorbent insertion elements 45 bind fluids that have been collected and are stored within the receiving region 34 for receiving fluids, so that a high wave movement of the fluid and therefore the overflowing of the fluid over the protective wall elements 38 is prevented during transportation and/or during movement of the patient support apparatus 30 and/or the table 31.

The patient support apparatus 30 also has a control unit 46, which is used to control movement of the patient support apparatus 30 and/or the table 31 during operation of the patient support apparatus 30. The control unit 46 here controls an approach speed of the patient support apparatus 30 and/or of the table 31, control taking place in such a manner that the overflowing and/or splashing over of a fluid present within the receiving region 34 for receiving fluids is prevented during the approach of the patient support apparatus 30 and/or of the table 31. The control unit 46 is disposed in a protected manner below the lower delimiting wall 37 within the support unit 32.

Figure 3:
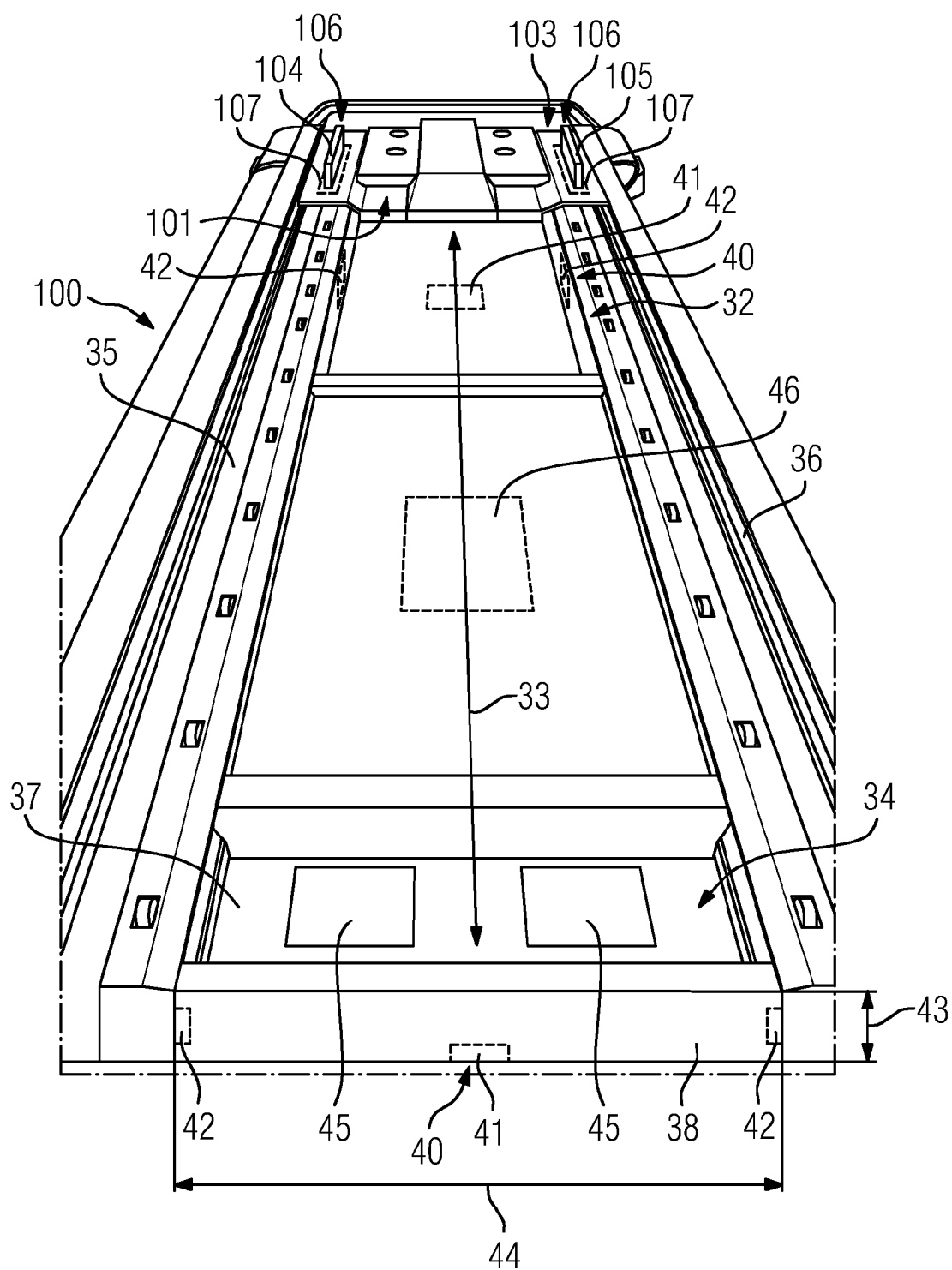
FIG. 3 shows a schematic diagram of an alternative embodiment of the patient support apparatus to the one in FIG. 2.

FIG. 3 shows an alternative exemplary embodiment of the patient support apparatus 100. Essentially identical components, features and functions are in principle shown with identical reference characters. The description which follows is essentially limited to the differences compared with the exemplary embodiment in FIGS. 1 and 2, reference being made to the description of the exemplary embodiment in FIGS. 1 and 2 in respect of identical components, features and functions.

The patient support apparatus 100 has a table 101 for positioning and supporting the patient 15 and a support unit 32 for supporting the table 101 in a movable manner.

In this embodiment, the table 101 has a receiving region 103 for receiving fluids. The table 101 has two protective wall elements 104, 105, which are disposed at the side next to a support region for supporting the patient 15. To dispose the protective wall elements 104, 105, the table 101 has a latching unit 106, which has individual latching units 107, which are configured in the same way as in the description of the exemplary embodiment relating to FIG. 2. When fluids are discharged from the patient 15 and/or from medical fittings, for example an infusion unit, these protective wall elements 104, 105 prevent said fluids spreading sideways over the table 101.

The support unit 32 is configured in the same way as in the description relating to FIG. 2, so that there is a flow of fluid from the receiving region 103 for receiving fluids on the table 101 into the receiving region 34 for receiving fluids within the support unit 32.

The patient support apparatus 100 of FIG. 3 may also be configured in such a manner that it only comprises a single receiving region 103 for receiving fluids, said receiving region 103 for receiving fluids being disposed on the table 101. In this instance the support unit 32 would be formed by a conventional support unit 32.

The patient support apparatuses 30, 100 may also have further structural units and/or elements, which are not illustrated in detail here. These further structural units and/or elements of the patient support apparatus 30, 100 are however known to the person skilled in the art so that there is no need for a more detailed description.

While specific embodiments have been described in detail, those with ordinary skill in the art will appreciate that various modifications and alternative to those details could be developed in light of the overall teachings of the disclosure. For example, elements described in association with different embodiments may be combined. Accordingly, the particular arrangements disclosed are meant to be illustrative only and should not be construed as limiting the scope of the claims or disclosure, which are to be given the full breadth of the appended claims, and any and all equivalents thereof. It should be noted that the term "comprising" does not exclude other elements or steps and the use of articles "a" or "an" does not exclude a plurality.

The invention claimed is:

1. A patient support apparatus, comprising:
    a table for supporting a patient, displaceable along a longitudinal direction to position the patient for imaging in a medical imaging apparatus,
    a support unit comprising spaced apart guide rails for supporting the table along the guide rails, the guide rails extending along the longitudinal direction such that the table is displaceable in the longitudinal direction along a longitudinal extension of the support unit,
    a receiving region for receiving fluids on the support unit, comprising a lower wall which delimits the receiving region in the direction of force of weight of received fluid, the receiving region delimited along first and second ones of the guide rails,
    one or more protective wall elements connectable to the support unit and extending between the first and second ones of the guide rails to further delimit and close off the receiving region to receive the fluids in a fluid-tight manner on the support unit, the one or more wall elements extending above the lower wall to prevent overflowing or splashing of fluid in the receiving region, and
    a plurality of latching elements each disposed on the support unit in different positions along the longitudinal direction to effect connection between the one or more wall elements and the support unit so that the one or more protective wall elements can be selectively disposed in different positions on the support unit to vary the size of the receiving region or divide the receiving region into multiple receiving chambers.

2. The patient support apparatus of claim 1, wherein the support unit has at least two protective wall elements which are disposed in different positions along the direction of the longitudinal extension on the support unit.

3. The patient support apparatus as claimed in claim 1, wherein the at least one or more protective wall elements are formed from a fluid-tight material.

4. The patient support apparatus as claimed in claim 1, wherein the one or more protective wall elements have a height which exceeds a multiple of an expected fluid level within the receiving region for receiving fluids.

5. The patient support apparatus as claimed in claim 4, wherein the one or more protective wall elements have a height of at least 3 cm.

6. The patient support apparatus as claimed in claim 1, wherein the at least one or more protective wall elements have a length which corresponds to a distance between the guide rails of the support unit.

7. The patient support apparatus as claimed in claim 1, further comprising:
    at least one absorbent insertion element which is disposed within the receiving region for receiving fluids.

8. The patient support apparatus as claimed in claim 1, further comprising:
    a control unit which controls a speed of the table and/or patient support apparatus for a movement of the table and/or patient support apparatus such that liquid fluid is prevented from overflowing over the one or more protective wall elements.

9. A medical imaging apparatus, comprising the patient support apparatus of claim 1.

* * * * *